United States Patent [19]

Karwacki, Jr. et al.

[11] Patent Number: 5,019,208

[45] Date of Patent: May 28, 1991

[54] METHOD FOR DETERMINING THE DEPTH OF PERMEATION OF A MODIFIER INTO THE INTERIOR OF A THERMOPLASTIC ARTICLE

[75] Inventors: Eugene J. Karwacki, Jr., Orefield; Fred M. Kimock, Macungie, both of Pa.

[73] Assignee: Air Products and Chemicals, Inc., Allentown, Pa.

[21] Appl. No.: 498,077

[22] Filed: Mar. 23, 1990

[51] Int. Cl.$^5$ .................. B44C 1/22; B29C 37/00; C03C 15/00; C03C 25/06
[52] U.S. Cl. .................................. 156/626; 156/651; 156/630; 156/633; 156/655; 156/668; 219/121.69; 219/121.83
[58] Field of Search ............... 156/626, 627, 630, 634, 156/651, 654, 655, 668, 633; 250/336.1; 356/307; 219/121.68, 121.69, 121.83, 121.85

[56] References Cited

U.S. PATENT DOCUMENTS 3,862,284 1/1975 Dixon et al. ..................... 264/83

FOREIGN PATENT DOCUMENTS 2160014 9/1984 United Kingdom .

OTHER PUBLICATIONS

J. Vac. Sci. Technol. A 4(3), May/Jun. 1986, J. T. C. Yeh, pp. 653–658.
J. Vac. Sci. Technol. A 4(6), Nov./Dec. 1986, Burrell, Lou and Cole, pp. 2459–2462.

Primary Examiner—William A. Powell
Attorney, Agent, or Firm—Keith D. Gourley; James C. Simmons; William F. Marsh

[57] ABSTRACT

A method for profiling the chemical structure and elemental composition as a function of distance below the exterior surface of a thermoplastic article, and more particularly, to a method for determining the depth of permeation of a modifier into the interior of a thermoplastic article which has been treated with the modifier. The method utilizes a pulsed ultraviolet energy source having a fluence level and pulse duration sufficient to ablate material from the article's exterior surface to a series of successive predetermined distances below the exterior surface to expose successive interior surfaces while causing essentially no physical or chemical damage to each respecting interior surface exposed by ablation. The elemental and chemical compositions of each successive interior surface are analyzed by a surface sensitive spectrographic technique and the spectrographic results are compared to determine the depth of modifier permeation within the thermoplastic article.

22 Claims, 7 Drawing Sheets

METHOD FOR DETERMINING THE DEPTH OF PERMEATION OF A MODIFIER INTO THE INTERIOR OF A THERMOPLASTIC ARTICLE

TECHNICAL FIELD

This invention relates to a method for profiling the chemical structure and elemental composition of a thermoplastic article as a function of distance below the exterior surface and more particularly, to a method for determining the depth of permeation of a modifier into the interior of a thermoplastic article which has been treated with the modifier.

BACKGROUND OF THE INVENTION

The near surface region of thermoplastic materials is often chemically modified to impart such materials with unique physical properties. Examples of surface-modified materials include binding materials which are coated with an adhesive layer, barriers or membranes which have been treated to facilitate gas separation or material containment and articles coated with corrosion-resistant materials.

Quality control in the manufacture of surface-modified thermoplastic articles is typically limited by the lack of a rapid, inexpensive method for determining the efficacy of surface treatment or polymer modification. Any practically useful test must be rapid, permitting the facile detection of variations in product uniformity and properties so that immediate corrective steps can be taken to eliminate such variations without necessitating termination of the process.

Assessing, monitoring and understanding the effect that such modifiers have on the interior composition and properties of surface modified thermoplastic articles requires characterization techniques capable of distinguishing variations in elemental composition and chemical structure as a function of depth within the interior of the article. The use of surface specific techniques such as X-Ray Photoelectron Spectroscopy (XPS), Auger Electron Spectroscopy (AES), Secondary Ion Mass Spectroscopy (SIMS) and high resolution Electron Energy Loss Spectroscopy (EELS) as qualitative techniques is often limited by the small volume of material sampled by the spectrographic method. Likewise, bulk sensitive techniques such as nuclear magnetic resonance, X-ray diffraction and infrared spectroscopy typically probe too deeply into, and below the surface to effect analysis of the near surface region and may physically damage the interior region under study.

An example of a surface-modified thermoplastic article is the AIROPAK ® surface-modified high density polyethylene container. AIROPAK is a registered trademark of Air Products and Chemicals, Inc., Allentown, PA. The AIROPAK container is manufactured by a blow molding process wherein a blowing gas containing about 0.1 to about 20% by volume fluorine is employed during the expansion stage of the process. Thermoplastic materials capable of being treated include polyolefin polymers and copolymers of ethylene, propylene, 1-butene, 1-pentene, 4-methyl-1-pentene, 3-methyl-1-butene and 3,3-dimethyl-1-butene. A process for making such containers is disclosed in U.S. Pat. No. 3,862,284 which is assigned to Air Products and Chemicals, Inc., Allentown, PA. Such surface treated bottles exhibit superior barrier performance to oils and other hydrocarbon liquids.

Attempts have been made to measure directly the permeability of surface-modified thermoplastic articles by exposing the surface of a barrier-coated thermoplastic article, or a sample cut therefrom, to a solution of an intensely colored or fluorescent dye, removing the article from the solution after a preset period of time and visually or instrumentally determining the degree and depth of dye permeation into the interior of the article. This method is suitable only for analysis of articles which are substantially free of interfering dark colored and/or opaque pigments which correlate with those of the colored or fluorescent dyes employed. Even when used for evaluation of articles free from interfering additives, these tests are sometimes unreliable.

Available indirect methods for testing the effectiveness of surface treatment include chemical or physical detection of active components in the barrier layers, for example, fluorine in AIROPAK containers. When fluorine is used as a surface-modifier, X-ray fluorescence, X-ray Photoelectron Spectroscopy (XPS) and combustion, followed by chemical analysis, can be utilized to analyze the surface of the article. The XPS technique employs a low energy X-ray source which dislodges core electrons of molecules or atoms residing near the surface of the specimen being analyzed thereby permitting specific analysis for elements residing on the surface of the specimen.

Other techniques for determining surface properties of thermoplastic articles include the measurement of contact angle or total reflectance. Multiple Internal Reflectance (MIR), which employs Fourier transform analysis of infrared data, is considered more reliable, but is too complex to be employed for routine determination of surface properties.

Methods for profiling the chemical structure and elemental composition of a thermoplastic article as a function of distance below the exterior surface are currently being used in the semiconductor industry. Such methods employ ion sputter etching, Angle-Resolved X-ray Photoelectron Spectroscopy and Rutherford Backscattering Spectrometry. Ion beam sputter depth profiling often results in physical and chemical damage to the sample causing particularly severe damage in non-metallic materials. Consequently, use of the technique as a means for determining chemical structure or elemental composition of thermoplastic materials as a function of distance below the exterior surface of the article is precluded. Depth resolution is often limited by effects such as primary ion knock-on and ion beam mixing which substantially hinder the ability to cleanly resolve thin layered structures within the solid.

Angle-Resolved X-ray Photoelectron Spectroscopy (ARXPS) is capable of probing the chemical structure of an article as a function of distance below the exterior surface, but only to depths of about 200 Angstroms. Thus, even though the technique maintains the integrity of the sample, the use of ARXPS technique is limited to analysis of the near-surface region. Source induced X-ray damage to the surface of the thermoplastic material can also occur during the extensive analysis time required to produce an ARXPS profile utilizing a multiple-anode X-ray source. While sample damage can be diminished by employing a monochromatic Al-Kα source, the analysis is then limited to a depth of about 150 Angstroms.

Rutherford Backscattering Spectrometry (RBS) yields compositional information as a function of depth and is a useful tool for analyzing the composition of thermoplastic articles to sub-surface depths up to about 2 microns. Moreover, RBS can be operated in a low ion dose mode to minimize sample damage. However, RBS does not provide chemical structural information and is limited to the detection of particular elements within the material.

A technique known as Laser Ablation Microprobe Mass Analysis (LAMMA) has been utilized for performing compositional profiles of numerous types of materials. In LAMMA. a tightly focused laser beam of long wavelength (typically > 500 nm) is directed onto the sample surface. The laser power density and wavelength are sufficient to produce intense local heating and ejection of ionized material from the surface. Because the intense local heating causes considerable structural damage to the material, use of the technique is limited to elemental composition profiling. The laser wavelength and power levels utilized in LAMMA have not, to date, been amenable to chemical profiling.

Current methods for analyzing the surface of thermoplastic materials include Great Britain Patent 2,160,014 B which relates to a method comprising directing a probe beam at the surface of the article to cause a sample of material to be removed therefrom., directing a non-resonant ionizing beam of radiation at the removed sample proximate the surface, the ionizing beam having an intensity sufficient to induce non-resonant photo-ionization of the sample whereby the sample is non-selectively ionized; and subjecting the ionized sample to mass-spectrometric analysis to determine the composition of the sample. Suitable probe beams for removing a sample from the surface are provided, for example, by an electron beam, an ion beam, a gas atom beam or a laser beam having a power density in the range of $10^6$ to $10^{12}$ W/cm$^2$.

Work conducted by J. T. C. Yeh. as reported in *J. Vac Sci. Technol. A* 4(3), May/June 1986, demonstrates that a wide variety of polymers can be ablated by short UV laser pulses. Such materials include polyethylene terephthalate, various polyimides, polymethyl methacrylate, polycarbonate, various photoresists, epoxy, human and animal hair and live tissue including cornea and cardiovascular tissues. Ablation is typically effected utilizing an excimer laser at a wavelength ranging from 193 to 351 nm. The reference further states that most polymeric materials can be etched cleanly using a laser at a wavelength of 193 nm and photon energy of 6.4 eV.

An article by Burrell. Lou and Cole, (*J. Vac. Sci. Technol. A*. Vol. 4, (6), Nov/Dec 1986), which is not prior art to the instant invention, suggests that laser ablation might be combined with X-ray photoelectron spectroscopy to provide compositional depth profiles of polymers such as polymethyl methacrylate which are not amenable to depth profiling by the usual ion-sputtering methods.

A need in the art exists for the development of a technique suitable for depth profiling the chemical structure and elemental composition of the interior of a thermoplastic article as well as a method for determining the depth of permeation of a modifier into the interior of a thermoplastic article which has been treated with a modifier.

SUMMARY OF THE INVENTION

The present invention relates to a method for profiling the chemical structure and elemental composition as a function of distance below the exterior surface of a thermoplastic article, and more particularly, to a method for determining the depth of permeation of a modifier into the interior of a thermoplastic article which has been treated with the modifier.

The method utilizes a pulsed ultraviolet energy source having a fluence level and pulse duration sufficient to ablate material from the exterior surface of the article to a series of successive predetermined distances below the exterior surface to expose successive interior surfaces while causing essentially no physical or chemical damage to each respective interior surface exposed by ablation. The elemental and chemical compositions of each successive interior surface are analyzed by a surface sensitive spectrographic technique and the spectrographic results are compared to determine the depth of modifier permeation within the thermoplastic article. Typical modifiers include dopants and surface treatments which regulate gas and liquid permeability.

A first embodiment relates to a method for profiling the elemental composition and chemical structure of a thermoplastic article as a function of distance below an exterior surface of the thermoplastic article. The process comprises (a) ablating the exterior surface of the thermoplastic article to a first predetermined distance below the exterior surface with a pulsed ultraviolet energy source having a fluence level and pulse duration sufficient to expose a first interior surface having a chemical structure and elemental composition which is substantially unaffected by the energy source;

(b) analyzing the elemental composition and chemical structure of the first interior surface by a surface sensitive spectrographic technique;

(c) ablating the first interior surface of the thermoplastic article to a subsequent predetermined distance by subjecting the first interior surface to the pulsed ultraviolet energy source to expose a successive interior surface;

(d) analyzing the elemental composition and chemical structure of the successive interior surface by a surface sensitive spectrographic technique;

(e) repeating steps (c) and (d) until reaching a final predetermined depth; and (f) correlating the elemental composition and chemical structure and elemental composition of each successive interior surface as a function of distance below the exterior surface to establish a profile of the elemental composition and chemical structure of the thermoplastic article.

In an alternate embodiment, a method is disclosed for determining the depth of permeation of a modifier into a thermoplastic article which has been exposed to the modifier. The method comprises ablating the exterior surface of the thermoplastic article to a first predetermined distance below the exterior surface by subjecting the thermoplastic article to a pulsed ultraviolet energy source having a fluence level and pulse duration sufficient to expose a first interior surface having a chemical structure and elemental composition which is substantially unaffected by the energy source; analyzing the elemental composition and chemical structure of the first interior surface by a surface sensitive spectrographic technique., ablating the first interior surface of the thermoplastic article to at least one additional predetermined distance below the exterior surface by subjecting the first interior surface to the pulsed ultraviolet energy source to expose a successive interior surface; analyzing the elemental composition and chemical structure of the successive interior surfaces by a surface sensitive spectrographic technique and comparing the elemental composition and chemical structure of the first interior surface and each successive interior surface to determine the depth of modifier permeation into the thermoplastic article.

The present invention provides a convenient quality control method for monitoring production of thermoplastic articles and provides a technique for profiling the elemental composition and chemical structure of various surface treated thermoplastic articles whereby the information illucidated from the analysis can be used to identify and differentiate the origin of surface-modified thermoplastic articles.

BRIEF DESCRIPTION OF THE DRAWINGS

FIGS. 5.1-5.5 are series of micrographs which illustrate the morphology of the inner surfaces of various surface-modified articles.

DETAILED DESCRIPTION OF THE INVENTION

The present invention relates to a method for profiling the chemical structure and elemental composition of a thermoplastic article, as a function of distance below the exterior surface and more particularly, to a method for determining the depth of permeation of a modifier into the interior of a thermoplastic article which has been treated with the modifier. The invention is uniquely capable of differentiating between in-situ and post-treatment modifications made to thermoplastic articles and has been demonstrated as a highly useful quality control method for monitoring the production of surface-modified thermoplastic articles.

The method for profiling the elemental composition and chemical structure of a thermoplastic article as a function of distance below the article's exterior surface utilizes a pulsed ultraviolet energy source having a fluence level and pulse duration sufficient to etch or ablate material from the exterior surface of the article to expose an interior surface having a chemical structure and elemental composition which is substantially unaffected by the energy source. More particularly, the exterior surface of the article is ablated to a series of successive predetermined depths followed by analysis of the elemental composition and/or chemical structure of each successive interior surface exposed by ablation. The depth of permeation of a modifier into the interior of a thermoplastic article can be readily deduced by comparing the elemental composition and chemical structure of the material at successively greater distances below the exterior surface of the thermoplastic article. The present invention is particularly suited for obtaining the structural and elemental profiles of thermoplastic articles which are highly susceptible to damage induced by the energetic ion beams typically used in conventional profiling techniques.

The present method differs significantly from approaches employed by known methods such as Laser Ablation Microprobe Mass Analysis (LAMMA) wherein the energy source utilized has a fluence up to 100 times greater whereby localized heating of the sample occurs resulting in substantial structural and chemical modifications to the article being analyzed. The combination of laser ablation and surface analysis extends the chemical and structural profiling capabilities of surface sensitive techniques to substantially greater distances below the exterior surface of surface-treated thermoplastic articles than achieved by methods known in the art. Techniques such as ion etching, fracturing and chemical etching all result in chemical and/or physical damage to the interfacial region.

A first embodiment relates to a method for profiling the elemental composition and chemical structure of a thermoplastic article as a function of distance below the article's exterior surface which comprises (a) ablating the exterior surface of the thermoplastic article to a first predetermined distance below the exterior surface with a pulsed ultraviolet energy source having a fluence level and pulse duration sufficient to expose a first interior surface having a chemical structure and elemental composition which is substantially unaffected by the energy source;

(b) analyzing the elemental composition and chemical structure of the first interior surface by a surface sensitive spectrographic technique;

(c) ablating the first interior surface of the thermoplastic article to a subsequent predetermined distance by subjecting the first interior surface to the pulsed ultraviolet energy source to expose a successive interior surface;

(d) analyzing the elemental composition and chemical structure of the successive interior surface by a surface sensitive spectrographic technique;

(e) repeating steps (c) and (d) until reaching a final predetermined depth; and (f) correlating the elemental composition and chemical structure and elemental composition of each successive interior surface as a function of distance below the exterior surface to establish a profile of the elemental composition and chemical structure of the thermoplastic article.

In an alternate embodiment, a method is disclosed for determining the depth of permeation of a modifier into the interior of a thermoplastic article which has been exposed to the modifier. The method comprises ablating the exterior surface of the thermoplastic article to a first predetermined distance below the exterior surface by subjecting the thermoplastic article to a pulsed ultraviolet energy source having a fluence level and pulse duration sufficient to expose a first interior surface having a chemical and structural composition which is substantially unaffected by the energy source; analyzing the elemental composition and chemical structure of the first interior surface by a surface sensitive spectrographic technique; ablating the first interior surface of the thermoplastic article to at least one additional predetermined distance below the exterior surface by subjecting the first interior surface to the pulsed ultraviolet energy source to expose a successive interior surface; analyzing the elemental composition and chemical structure of the successive interior surfaces by a surface sensitive spectrographic technique and comparing the elemental composition and chemical structure of the first interior surface and each successive interior surface to determine the depth of modifier permeation into the thermoplastic article.

In each of the above-mentioned embodiments, a pulsed ultraviolet energy source is focused, either by lensing or masking, onto the exterior surface of the thermoplastic article to be analyzed. Typically, the thermoplastic article is subjected to about 1 to about 10,000 pulses of an ultraviolet energy source having a wavelength ranging from 100 nm to about 340 nm and a fluence level ranging from about 20 to about 750 millijoules/$cm^2$. Ablation is continued until the material is ablated to a predetermined depth thereby exposing a first interior layer of the thermoplastic article. The amount of material that is ablated from the exterior surface of the thermoplastic article is controlled by varying the fluence level and number of pulses of the ultraviolet energy source. Table 1 illustrates the fluence level and number of pulses typically required to ablate or remove various amounts of material from the exterior-most surface of the sample.

TABLE 1

CORRELATION OF FLUENCE LEVEL AND ABLATION DEPTH

| Pulses | Wavelength (nm) | Analysis Depth (um) | Fluence(mJ/$cm^2$) |
|---|---|---|---|
| 0–10,000 | 100–340 | 0–100 | 20–500 |
| 0–100 | 150–308 | 0–5 | 20–150 |
| 0–25 | 150–240 | 0–1 | 35–75 |

A threshold level of the pulsed ultraviolet energy source is utilized, i.e., that amount which is sufficient to cause photochemical bond breaking within the near surface region whereby atomic and molecular fragments of the thermoplastic article are ejected from the surface of the sample. A crater is left behind as a result of the ejection of material. The depth of the crater is a function of the laser power density, the number of laser pulses incident on the sample and the sample matrix.

Suitable ultraviolet energy sources for practicing the present invention are well known in the art and include excimer lasers, solid state lasers, dye lasers, flash tubes and the like. In a preferred embodiment, an excimer laser is utilized as an ultraviolet energy source.

A sample holder has been designed to facilitate the practice of the present invention. This device is a multi-sample position holder which is mounted onto the optical ablation bench and which can be introduced subsequently into the spectrometer. More particularly, the device resembles a slide rule wherein the center plate is sectioned to hold up to 20 samples. This center plate region can be removed from the platen and mounted directly in the spectrometer. The center plate can be actuated to expose a new sample to ablation or spectroscopic analysis without dismantling the apparatus.

Identical samples are aligned along the center plate. While the size of the sample to be analyzed may vary, a typical sample size is about 4×4 mm. Ablation of a 2 mm diameter region is performed. Difficulty is sometimes experienced in locating the crater for analysis when the sample is transferred to a spectrometer. Alternately, a 2×2 mm sample has been employed wherein the entire sample surface is ablated. The mounted samples are individually aligned with the laser spot and exposed to the desired number of laser pulses.

An alternate embodiment may be utilized wherein an in-situ method is utilized. The laser beam is focussed through a viewport onto the sample which is held within the analysis chamber. Analysis is then immediately performed wherein laser pulsing and spectral analysis are sequentially effected by computer control. Only one sample is needed to perform a complete depth analysis utilizing this embodiment.

The laser ablation depth can be determined by a variety of methods. For example, the total ablation depth can be ascertained via diamond stylus profilometry or ellipsometry, methods which are well known in the art. Another suitable approach involves comparison of the results obtained by X-ray photoelectron spectroscopy to those obtained from Rutherford Backscattering Spectrometry (RBS) measurements. RBS is a technique capable of measuring the thickness of thin films. The measurement of etch depth in thermoplastic materials is easily performed by those of ordinary skill in the art. Following ablation, the mounted samples are transferred to a spectrometer wherein a separate surface analysis is performed on each sample.

The particular spectrometric technique to be utilized depends upon the thermoplastic material and the type and composition of the modifier. Moreover, certain surface sensitive techniques are more particularly adapted toward the analysis of the elemental composition of the surface as opposed to the chemical composition of the sample. Surface sensitive techniques utilized to analyze the elemental composition of each successive interior surface include Auger electron spectroscopy, ion scattering spectrometry, high resolution electron energy loss spectroscopy, X-ray photoelectron spectroscopy and secondary ion mass spectrometry. The chemical structure of each successive interior surface is most often illucidated by the use of X-ray photoelectron spectroscopy, Raman spectroscopy or electron energy loss spectroscopy.

In the final step of the process, the elemental composition and chemical structure of each of the succesive interior surfaces are correlated as a function of depth to establish a profile of the elemental composition and chemical structure of the thermoplastic article, or alternately, the depth of permeation of a modifier into the interior of the article.

The use of pulsed ultraviolet excimer laser energy to remove material from the surface of the thermoplastic article provides numerous advantages over methods known in the art. For example, laser ablation under controlled conditions affords the ability to produce large e.g., greater than 5 mm diameter craters with flat bottom and sharp walls. Consequently, minimal structural rearrangements to the composition of the sample occur in, or within proximity of the crater and minimal morphological damage occurs to the crater thereby minimizing mixing of atomic layers. Various depths ranging from Angstroms to microns per laser pulse can be effected by varying laser power. These results are in contrast to those obtained by etching via ion beam sputtering wherein poor crater morphology is realized and considerable chemical damage occurs to the material.

Thermoplastic articles which can be analyzed according to the present invention vary widely in both composition and structure. For purposes of interpreting the appended Claims, the term, thermoplastic article shall include films, plaques, bottles, drums and any other article comprised of a thermoplastic material which is capable of being treated with the modifiers disclosed herein.

The thermoplastic articles can consist of phenolics, aminoplastics, epoxy resins, polyesters, silicones, polyolefins, polystyrene, polyvinyl plastics, fluorocarbon-containing polyolefins, polycarbonates, polyamides, polyacetals, polyacrylates, polyphenylene oxides, polysulfones, polyurethanes and cellulosics, including homopolymers, copolymers, grafted copolymers and blends of any of the foregoing.

When reference is made to a polyolefin polymer, such polymers refer to the polymerization products of linear or branched alkylenes having from 1 to about 10 carbon atoms and include homopolymers, copolymers, blends, and mixtures thereof, of ethylene, propylene, 1-butene, 1-pentene, 4-methyl-1-pentene, 3-methyl-1-butene and 3,3-dimethyl-1-butene. It is understood that the preceding list of polymers is descriptive and shall not be deemed limiting with reference to the thermoplastic materials capable of being profiled according to the present invention.

Modifiers according to the present inventions include dopants, stabilizers, adhesives, pigments, fillers, delustrants, plasticizers, flame retardants, antistatic agents and other materials known in the art to modify the chemical and physical properties of thermoplastic articles. Representative surface-modified thermoplastic articles include semi-permeable membranes, polyolefins which have been surface treated with fluorine and laminates comprising a plurality of layers of thermoplastic materials, each which may be mechanically joined by an adhesive.

An alternate embodiment of the invention relates to a method for determining the extent of permeation of a modifier into a thermoplastic article which has been exposed to the modifier. This embodiment provides a convenient method for monitoring quality control during the manufacture of surface-modified thermoplastic articles. An example of such a surface-modified thermoplastic article is the AIROPAK fluorine-treated high density polyethylene bottle. Well-fluorinated containers possess a chemical composition and elemental analysis as a function of distance below the sample's exterior surface which differs greatly from poorly treated containers. The effective fluorination of high density polyethylene results in the replacement of a significant number of hydrogen atoms, as from the polymer backbone, by fluorine up to a depth of about 400–500 Å. In contrast, poorly treated polyethylene containers possess lesser amounts of fluorine in the polymer backbone and the depth of fluorine penetration into the article is limited.

The following examples illustrate various embodiments of the present invention and are not intended to limit the scope of the appended claims.

These Examples illustrate the use of the present invention for profiling the chemical structure and elemental composition of two thermoplastic articles prepared under different conditions and assessing the depth of permeation of a modifier, i.e., fluorine, into the interior of the articles. The information ellucidated from the analysis of these samples will then be used to identify and differentiate the origin of each article.

EXAMPLE 1

Depth Profiling of an AIROPAK High Density Polyethylene Bottle

This example illustrates a method for determining the chemical structure and elemental composition of an AIROPAK high density polyethylene bottle which was prepared according to the procedure enumerated in U.S. Pat. No. 3,862,284. The sample was ablated with an unfocused beam from a Lambda Physik EMG101MSC excimer laser operated on the ArF 193 nm line. Laser conditions included a pulse duration of approximately 20 ns, repetition rate of 1 Hz, normal incidence, circular spot size of 0.3 $cm^2$, and an energy density of 75 $mJ/cm^2$. Six samples were cut from the bottle and ablated in air with 0, 25, 50, 75 and 100 laser pulses, respectively. Following the laser ablation, all samples were inserted into a Physical Electronics 5000LS X-Ray photoelectron spectrometer and analyzed with a spot size of 1.1 mm imaged from the center of each crater. The depth of each crater was measured by performing Rutherford Backscattering Spectrometry on each sample prior to spectrometric analysis. The carbon 1s spectrum was deconvoluted using a curve fitting algorithm. From such a mathematical model, the various function group contributions to the spectrum were quantified. The C 1s spectrum was fitted with five peaks representing the following species: $CH_x$, $CH_x$—$CF_x$, CHF, $CF_2$ and $CF_3$.

EXAMPLE 2

Depth Profiling of a Post-Fluorinated High Density Polyethylene Bottle

This Example illustrates a method for determining the chemical structure and elemental composition of a high density polyethylene bottle which was post-treated by a 5 minute treatment with a 1% fluorine/99% nitrogen gas blend. The experimental procedure enumerated in Example 1 was utilized to analyze the sample.

The XPS carbon 1s spectrum of fluorinated polyethylene prior to laser ablation (0 laser pulses) shows the following carbon species to be present on the surface: $CF_3$ (293.9 eV), $CF_2$ (291.2 eV), CF (288.8 eV), $CH_x$—$CF_x$ (286.4 eV) and $CH_x$-$CH_x$ (285.0 eV). All peak assignments are based on charge correction of the CHx-CHx line to 285.0 eV binding energy. Graphic representations of the elemental composition of a sidewall from an AIROPAK bottle according to Example 1 and a post-fluorinated polyethylene bottle according to Example 2, as a function of distance below the exterior surface are presented in FIGS. 1 and 2, respectively. The relative atomic percent distribution for carbon (C), oxygen (0) and fluorine (F) are plotted versus depth. As previously stated, the depth was measured by performing Rutherford Backscattering Spectrometry on each material prior to spectral analysis.

Figure 1:
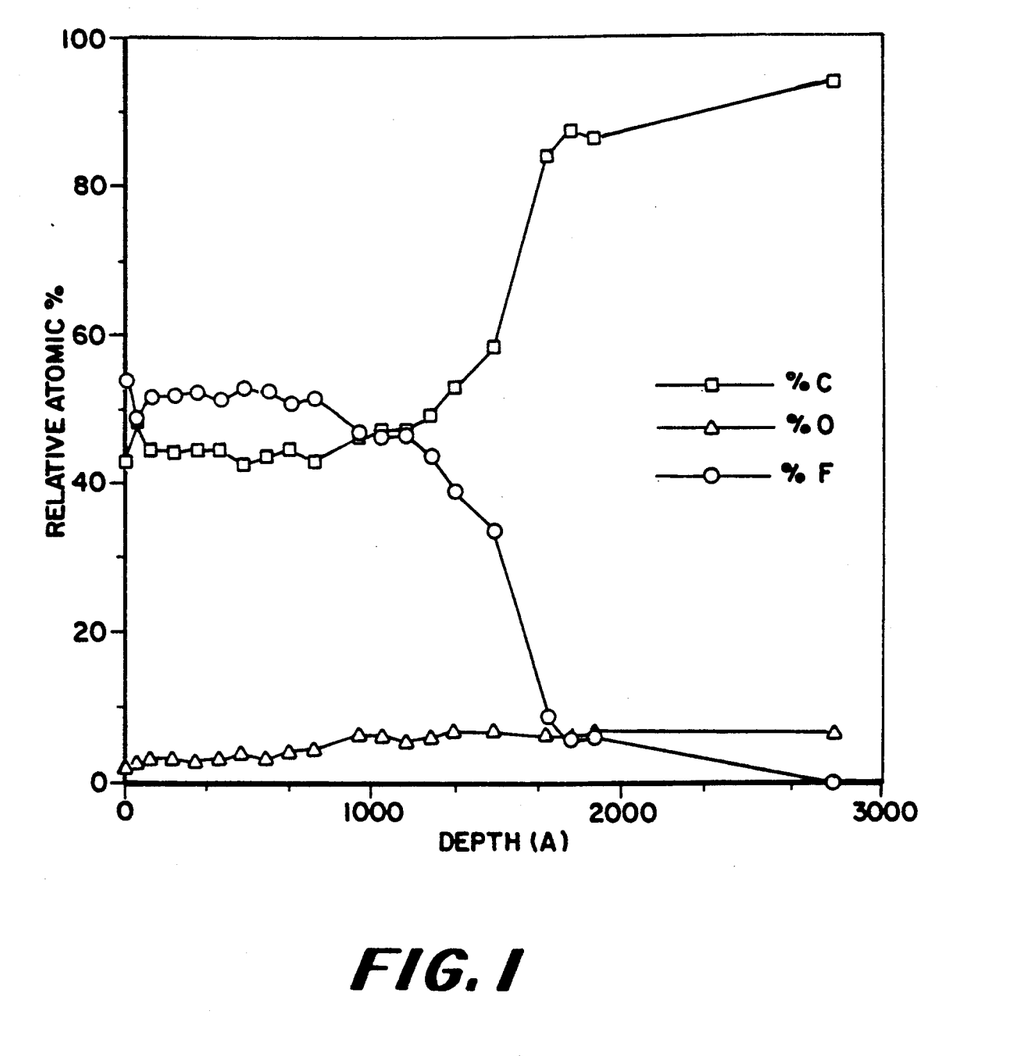
FIG. 1 is a graphic representation of the elemental composition of an AIROPAK bottle as a function of distance below the exterior surface of the bottle.
Figure 2:
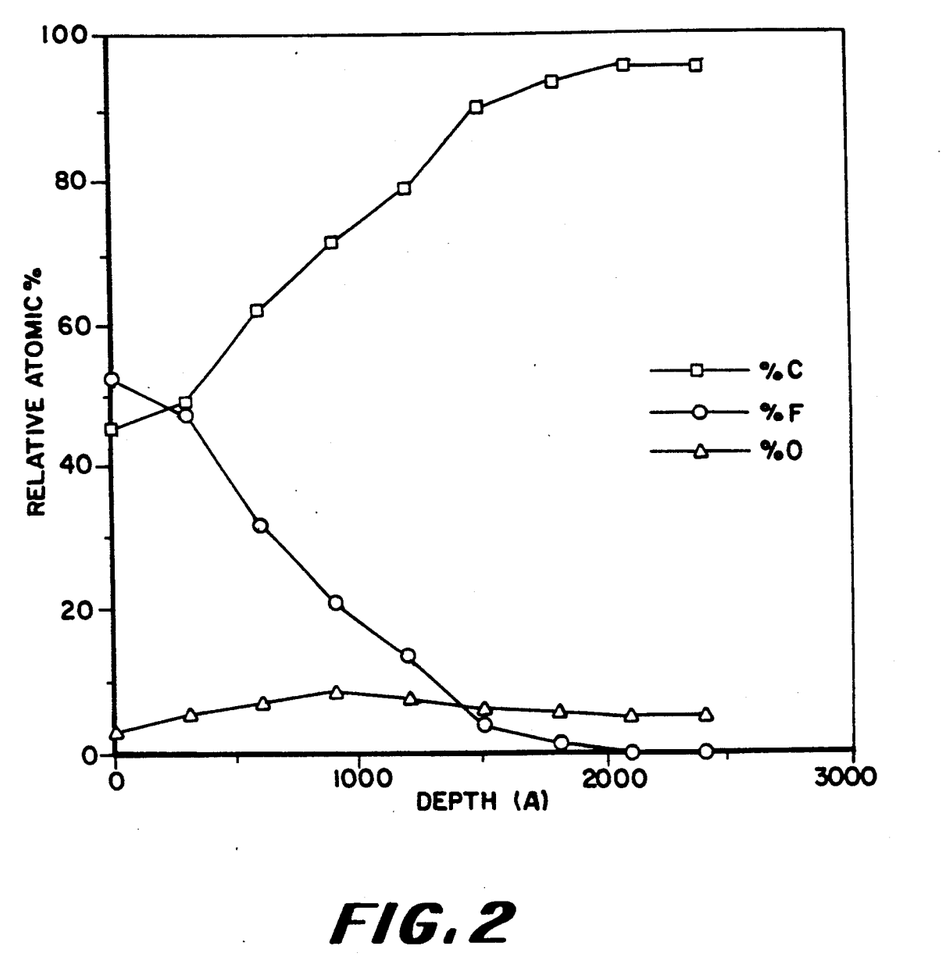
FIG. 2 is a graphic representation of the elemental composition of a post-fluorinated polyethylene bottle as a function of distance below the exterior surface of the bottle.

With respect to characterizing AIROPAK treated bottles, these LAXPS profiles clearly demonstrate that the AIROPAK process produces a uniform treatment over the depth to which the article was fluorinated. In contrast, the post-fluorinated article is characterized by the absence of uniform composition at each respective distance below the exterior surface. The method according to the present invention provides a convenient method for determining the compositional profile of a thermoplastic article as well as a method for determining the extent of permeation of a modifier, in this case fluorine, into the interior of an article.

Figure 3:
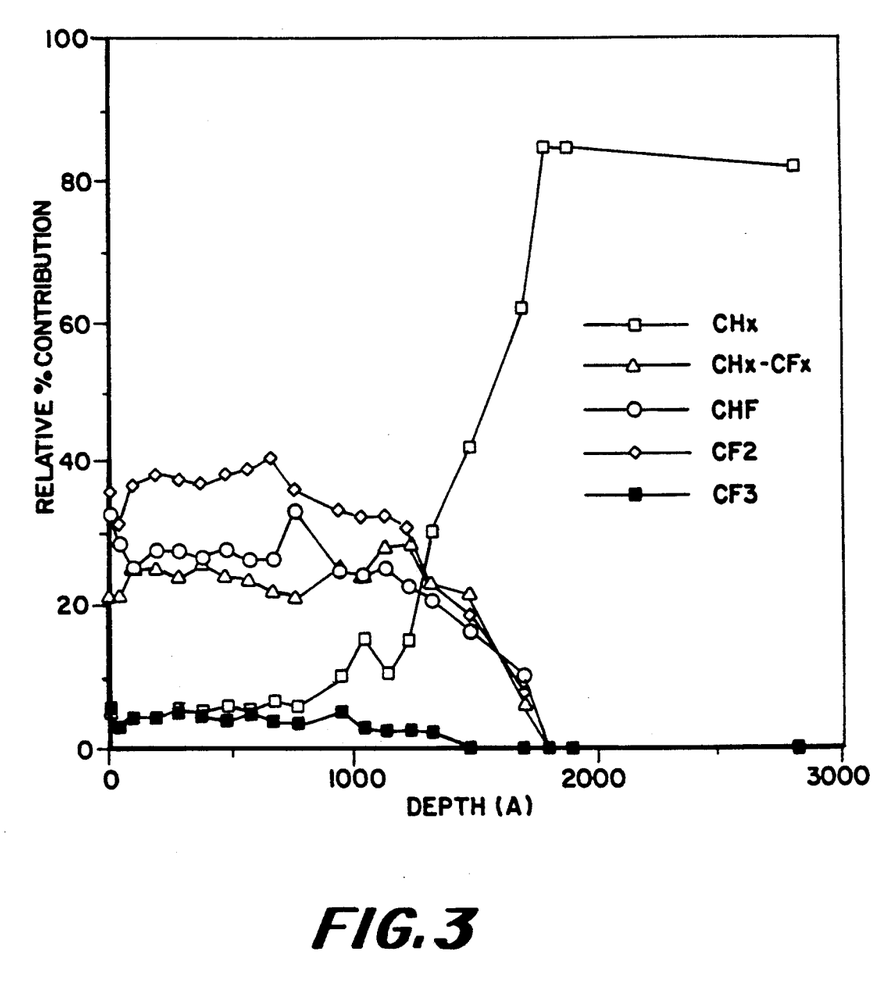
FIG. 3 is a graphic representation of the structural profile of an AIROPAK bottle as a function of distance below the exterior surface of the bottle.
Figure 4:
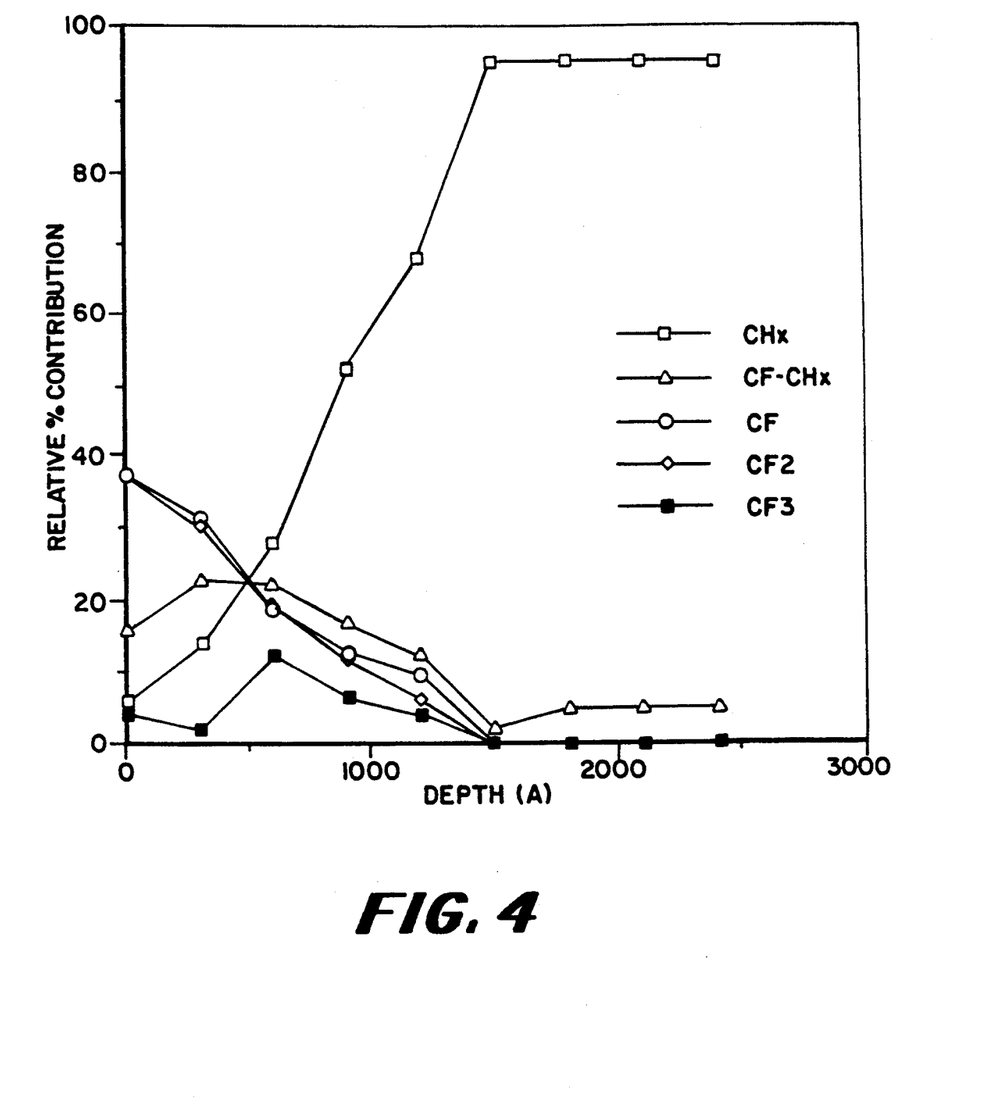
FIG. 4 is a graphic representation of the structural profile of a post-fluorinated polyethylene bottle as a function of distance below the exterior surface of the bottle.

FIGS. 3 and 4 disclose a structural profile of the above-mentioned bottles as a function of distance below the external surface of the sidewall from an AIROPAK bottle according to Example 1 and a post-fluorinated polyethylene bottle according to Example 2, respectively. Comparison of FIGS. 3 and 4 demonstrates that the AIROPAK polyethylene bottle exhibits essentially uniform composition at successive depths to at least 1500 Angstroms below the exterior surface. More particularly, the relative percentage contribution of fluorinated and polyfluorinated alkyl and alkylene linkages is uniform in each of the successive, interior surfaces. In contrast, the post-fluorinated polyethylene bottle according to Example 2 demonstrates non-uniform relative percentage contribution of fluorinated species as a function of depth within the sample's interior. The absence of uniformity suggests a method of preparation which differs from the AIROPAK bottle according to Example 1 and provides evidence of inferior barriers characteristics due to the absence of uniform fluorination.

EXAMPLE 3

Method for Determining the Source of a Surface-treated Polyethylene Bottle

Figure 51:
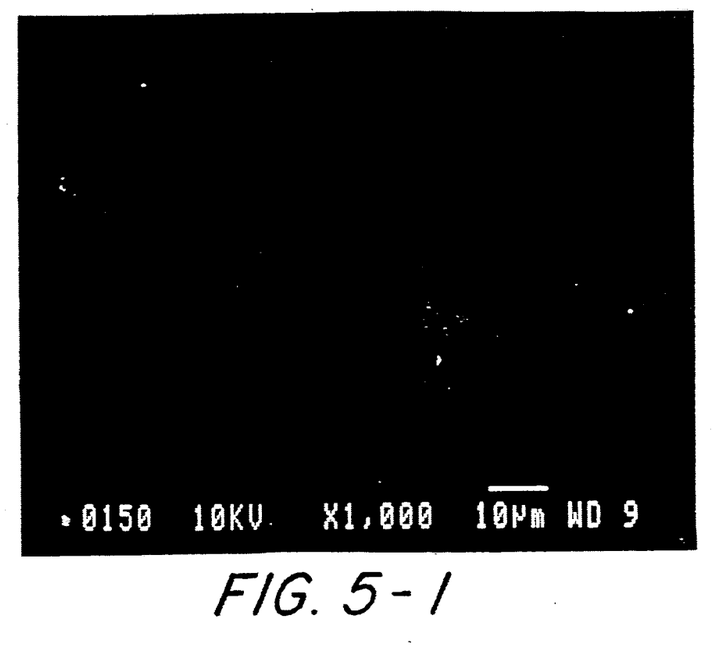
Figure 52:
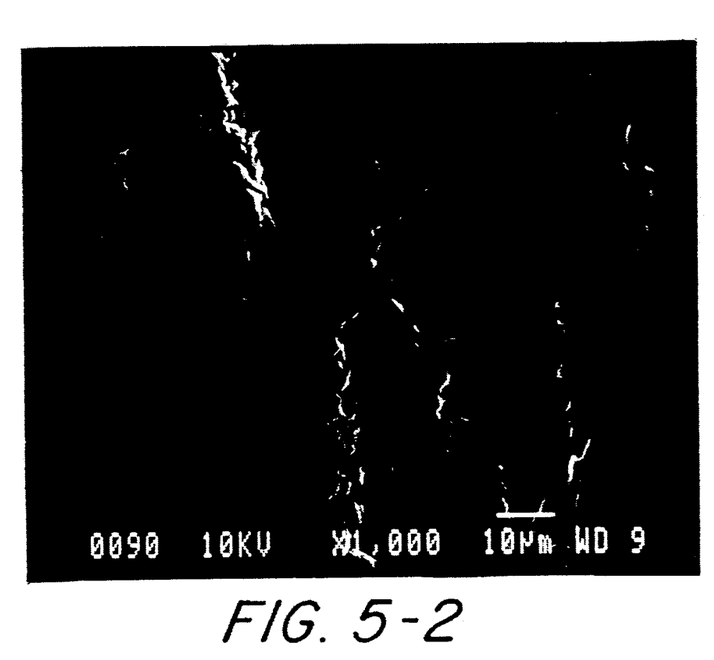
Figure 53:
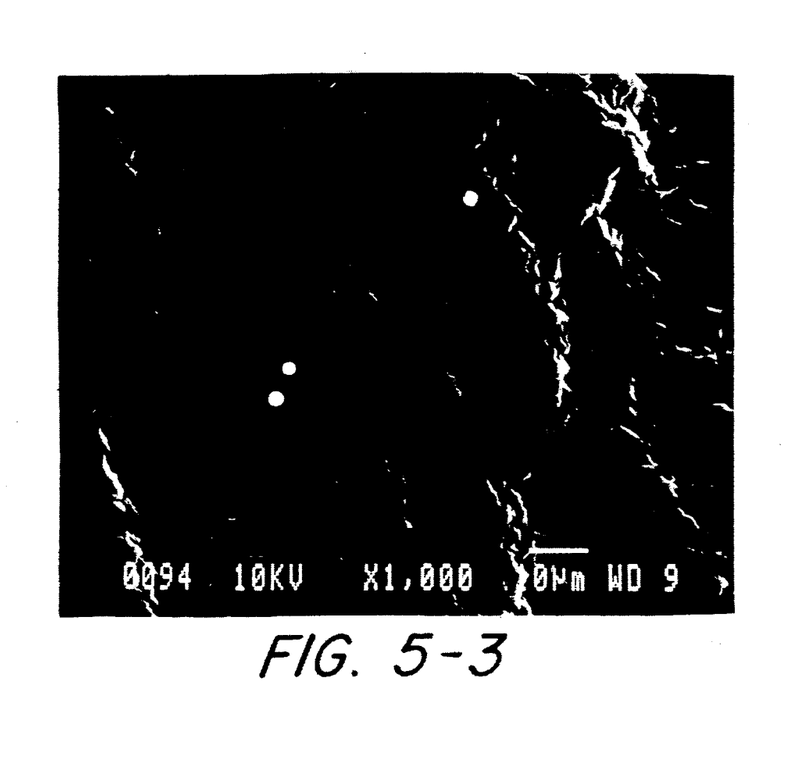
Figure 54:
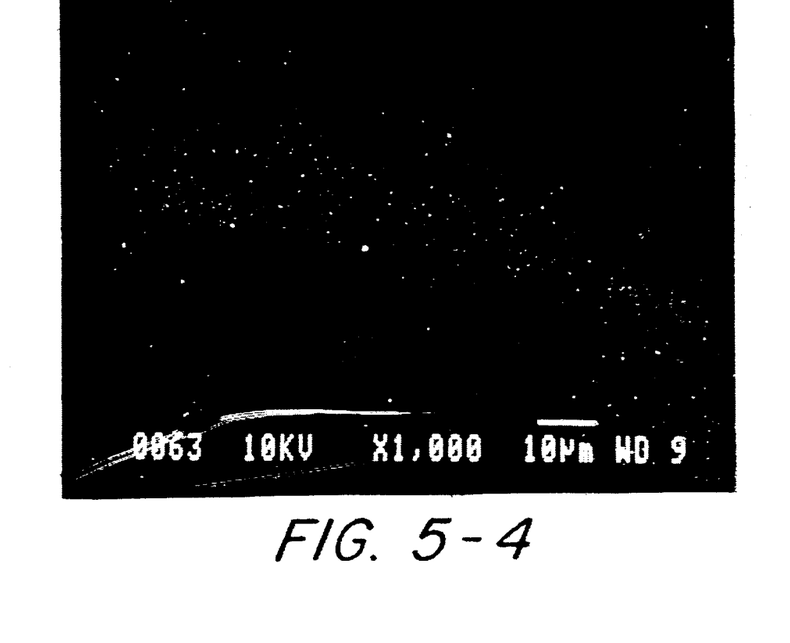

In addition to chemically modifying the near-surface region of polyethylene. The AIROPAK process, as previously described, also imparts a novel surface morphology. This characteristic provides a convenient route for determining the source of a surface-treated polyethylene bottle. Referring to the micrographs of FIG. 5, micrograph 5-1 illustrates the morphology of an inner surface of a polyethylene bottle manufactured by a process utilizing nitrogen gas as the sole blowing agent wherein a very smooth and nondescript surface is observed. Micrograph 5-2 illustrates the inner surface of an identical polyethylene bottle blown using the AIROPAK process wherein the presence of fluorine within the blow gas initiates a change in the polyethylene morphology. This unique morphology is not observed in bottles which are blown with nitrogen and then post-treated with fluorine.

The samples illustrated in micrographs 5-1 and 5-2 were then subjected to 15 pulses of an excimer laser (under the conditions disclosed in Example 1). Micrograph 5-3 shows a scanning electron micrograph of the AIROPAK polyethylene bottle wherein the interior layer has a morphology similar to the surface morphology presented in micrograph 5-1. Micrograph 5-4 illustrates the AIROPAK sample following treatment with 5000 pulses of the excimer laser wherein the morphology has returned the smooth, nondescript appearance that was observed in micrograph 5-1.

Figure 55:
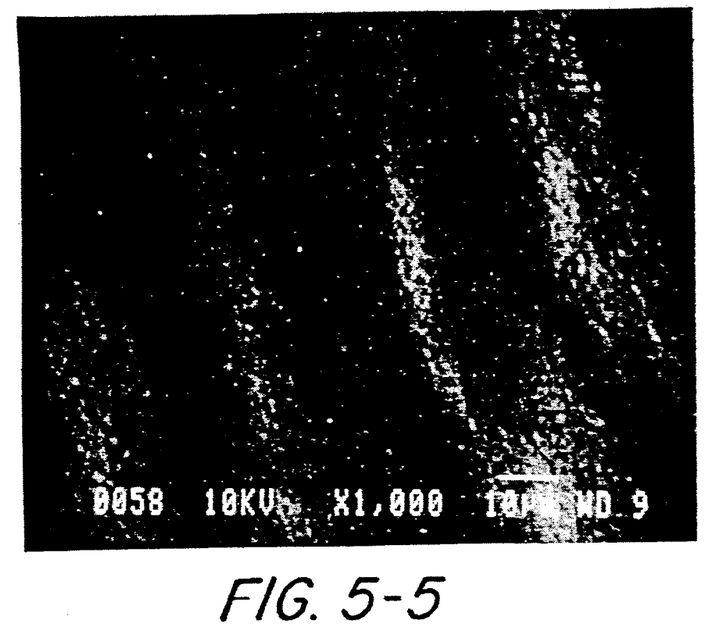

To further demonstrate that laser ablation does not impart thermal damage to the polyethylene articles, the polyethylene bottle manufactured using nitrogen gas only, was subjected to 500 pulses of an excimer ultraviolet energy source micrograph 5-1. Comparison of micrographs 5-1 and 5-5 demonstrates that the only change in morphology is the loss of very fine micromorphology due to cooling which occurred following the initial blowing molding process. This fine micromorphological difference can be detected only under very high magnification (greater than 7500×).

The present invention provides a convenient quality control method for monitoring production of thermoplastic articles and provides a technique for profiling the elemental composition and chemical structure of various surface treated thermoplastic articles whereby the information illucidated from the analysis can be used to identify and differentiate the origin of surface modified thermoplastic articles.

Having thus described the present invention, what is now deemed appropriate for Letters Patent is set out in the following appended Claims.

We claim:
1. A method for profiling the elemental composition and chemical structure of a thermoplastic article as a function of distance below an exterior surface of the thermoplastic article comprising:
   (a) ablating the exterior surface of the thermoplastic article to a first predetermined distance below the exterior surface with a pulsed ultraviolet energy source having a fluence level and pulse duration sufficient to expose a first interior surface having a chemical structure and elemental composition which is substantially unaffected by the energy source;
   (b) analyzing the elemental composition and chemical structure of the first interior surface by a surface sensitive spectrographic technique;
   (c) ablating the first interior surface of the thermoplastic article to a subsequent predetermined distance by subjecting the first interior surface to the pulsed ultraviolet energy source to expose a successive interior surface;
   (d) analyzing the elemental composition and chemical structure of the successive interior surface by a surface sensitive spectrographic technique;
   (e) repeating steps c and d until reaching a final predetermined depth; and
   (f) correlating the elemental composition and chemical structure and elemental composition of each successive interior surface as a function of distance below the exterior surface to establish a profile of the elemental composition and chemical structure of the thermoplastic article.

2. The method according to claim 1 wherein the surface sensitive technique utilized to analyze the elemental composition of each successive surface is selected from Auger electron spectroscopy, ion scattering spectrometry, high resolution electron energy loss spectroscopy. X-ray photoelectron spectroscopy or secondary ion mass spectrometry.

3. The method according to claim 2 wherein the surface sensitive technique utilized to analyze the chemical structure of each successive surface is selected from X-ray photoelectron spectroscopy, Raman spectroscopy or electron energy loss spectroscopy.

4. The method according to claim 3 wherein the thermoplastic article is subjected to 1 to about 10,000 pulses of the ultraviolet energy source having a wavelength ranging from 100 nm to about 340 nm and a fluence level ranging from 20 to about 750 millijoules/cm$^2$.

5. The method according to claim 4 wherein the thermoplastic article is subjected 1 to about 100 pulses of the ultraviolet energy source having a wavelength ranging from 150 nm to about 310 nm and a fluence level ranging from 20 to about 150 millijoules/cm$^2$.

6. The method according to claim 4 wherein the thermoplastic article is a laminate comprising a plurality of layers of thermoplastic material.

7. The method according to claim 6 wherein the plurality of layers are mechanically joined by an adhesive.

8. The method according to claim 4 wherein the thermoplastic article is a semi-permiable membrane.

9. The method according to claim 4 wherein the thermoplastic article is a polyolefin which has been surfaced treated with fluorine.

10. The method according to claim 4 wherein the polyolefin is a polymerization product of linear or branched alkylenes having from 1 to about 10 carbon atoms.

11. The method according to Claim 10 wherein the polyolefin is a high density polyethylene.

12. A method for determining the depth of permeation of a modifier into a thermoplastic article having an exterior surface which has been exposed to the modifier comprising:
(a) ablating the exterior surface of the thermoplastic article to a first predetermined distance below the exterior surface by subjecting the thermoplastic article to a pulsed ultraviolet energy source having a fluence level and pulse duration sufficient to expose a first interior surface having a chemical and structural composition which is substantially unaffected by the energy source;
(b) analyzing the elemental composition and chemical structure of the first interior surface by a surface sensitive spectrographic technique and
(c) ablating the first interior surface of the thermoplastic article to at least one additional predetermined distance below the exterior surface by subJecting the first interior surface to the pulsed ultraviolet energy source to expose a successive interior surface;
(d) analyzing the elemental composition and chemical structure of the successive interior surfaces by a surface sensitive spectrographic technique and
(e) comparing the elemental composition and chemical structure of the first interior surface and each successive interior surface to determine the depth of modifier permeation into the thermoplastic article.

13. The method according to claim 12 wherein the surface sensitive technique utilized to analyze the elemental composition of each successive surface is selected from Auger electron spectroscopy, ion scattering spectrometry, high resolution electron energy loss spectroscopy, X-ray photoelectron spectroscopy or secondary ion mass spectrometry.

14. The method according to claim 13 wherein the surface sensitive technique utilized to analyze the chemical structure of each successive surface is selected from X-ray photoelectron spectroscopy, Raman spectroscopy or electron energy loss spectroscopy.

15. The method according to claim 14 wherein the thermoplastic article is subjected to 1 to about 10,000 pulses of the ultraviolet energy source having a wavelength ranging from 100 nm to about 340 nm and a fluence level ranging from 20 to about 750 millijoules/cm$^2$.

16. The method according to claim 15 wherein the thermoplastic article is subjected 1 to about 100 pulses of the ultraviolet energy source having a wavelength ranging from 150 nm to about 310 nm and a fluence level ranging from 20 to about 150 millijoules/cm$^2$.

17. The method according to claim 15 wherein the thermoplastic article is a laminate comprising a plurality of layers of thermoplastic material.

18. The method according to claim 17 wherein the plurality of layers are mechanically joined by an adhesive.

19. The method according to claim 15 wherein the thermoplastic article is a semi-permiable membrane.

20. The method according to claim 15 wherein the thermoplastic article is a polyolefin which has been surfaced treated with fluorine.

21. The method according to claim 15 wherein the polyolefin is a polymerization product of linear or branched alkylenes having from 1 to about 10 carbon atoms.

22. The method according to claim 21 wherein the polyolefin is a high density polyethylene.

* * * * *